United States Patent [19]
Spence et al.

[11] Patent Number: 6,124,487
[45] Date of Patent: Sep. 26, 2000

[54] OLEFIN POLYMERIZATION CATALYST HAVING A BRIDGED PHOSPHOLE-HETEROATOM LIGAND

[75] Inventors: Rupert Edward von Haken Spence; Xiaoliang Gao; Linda Koch; Stephen John Brown; Daryll G. Harrison, all of Calgary, Canada

[73] Assignee: Nova Chemicals (International) S.A., Switzerland

[21] Appl. No.: 09/036,241

[22] Filed: Mar. 6, 1998

[30] Foreign Application Priority Data

Mar. 19, 1997 [CA] Canada .................................. 2200373

[51] Int. Cl.[7] ................................ C07F 15/00; C07F 9/02
[52] U.S. Cl. ................................ 556/11; 556/12; 556/30; 556/52; 556/64; 568/12; 106/901; 526/90; 502/152; 502/117; 502/162; 502/158
[58] Field of Search ..................................... 502/152, 117, 502/162, 158; 526/90; 106/901; 568/12; 556/64, 11, 12, 30, 52

[56] References Cited

U.S. PATENT DOCUMENTS

| | | | |
|---|---|---|---|
| 4,404,344 | 9/1983 | Sinn et al. | 526/160 |
| 4,542,199 | 9/1985 | Kominsky et al. | 526/160 |
| 5,055,438 | 10/1991 | Canich | 502/117 |
| 5,057,475 | 10/1991 | Canich et al. | 502/104 |
| 5,096,867 | 3/1992 | Canich | 502/103 |
| 5,132,380 | 7/1992 | Stevens et al. | 526/126 |
| 5,153,157 | 10/1992 | Hlatky et al. | 502/117 |
| 5,198,401 | 3/1993 | Turner et al. | 502/155 |
| 5,227,440 | 7/1993 | Canich et al. | 526/129 |
| 5,374,696 | 12/1994 | Rosen et al. | 526/126 |
| 5,387,568 | 2/1995 | Ewen et al. | 502/104 |
| 5,399,635 | 3/1995 | Neithemer et al. | 526/126 |
| 5,407,884 | 4/1995 | Turner et al. | 502/155 |
| 5,434,116 | 7/1995 | Sone et al. | 502/103 |

FOREIGN PATENT DOCUMENTS

| | | |
|---|---|---|
| 416815 | 3/1991 | European Pat. Off. . |
| 423872 | 4/1991 | European Pat. Off. . |
| 0617052A2 | 9/1994 | European Pat. Off. .......... C08F 4/52 |
| 0741145A1 | 11/1996 | European Pat. Off. ...... C08F 10/100 |
| WO9504087 | 2/1995 | WIPO ................................ C08F 4/60 |

OTHER PUBLICATIONS

Metallacycle Transfer from Zinconium to Main Group Elements: A Versatile Synthesis of Heterocycles. Paul J. Fagan, William A. Nugent and Joseph C. Calabrese 1994 American Chemical Society, 116 pages 1880–1889.

The Synthesis and Reactionty of Monocyclepentadiecyl Scandium Amide and Acetylacetonato Derivatives, Pamela J. Shipiro and John Bercaw, Dept. of Chemistry, California Institute of Technology, Pasadena, California 91125.

The Influence of Electronic and Steric Effects and the Importance of Polymerization Conditions in the Ethylene Polymerization with Zirconcene/MAO Catalysts, Christopher Janiak, Uwe Versteeg, Katharina C.H. Lange, Roman Weimann, Ekkehardt Hahn, Journal of Organometalic Chemistry 501 (1995) 219–234.

*Primary Examiner*—Yogendra Gupta
*Assistant Examiner*—Charles Boyer
*Attorney, Agent, or Firm*—Kenneth H. Johnson

[57] ABSTRACT

A new family of metallacycles, which are preferably zirconacycles, is characterized by having a unique halogenated substituent. The metallacycles are useful for the preparation of main group heterocycles, especially two novel families of heterocycles. The first new family of heterocycles preferably contains a halosilyl substituent. A preferred group of the second family of novel heterocycles contains a silyl group having a leaving group bonded thereto. The preferred group of these heterocycles is suitable for preparing novel organometallic complexes having a bridged bidentate heterocyclic ligand. These novel organometallic complexes may be used as catalyst components in olefin polymerization. The subject catalyst components are particularly well suited for use in the medium pressure solution process to prepare linear low density polyethylene.

11 Claims, No Drawings

OLEFIN POLYMERIZATION CATALYST HAVING A BRIDGED PHOSPHOLE-HETEROATOM LIGAND

FIELD OF THE INVENTION

This invention relates to a new metallacycle family; the preparation of new main group heterocycles from the metallacycles; the preparation of new, dianionic bridging heterocyclic ligands and the use of organometallic complexes containing these ligands in olefin polymerizations.

BACKGROUND

The synthesis of main group heterocycles such as boroles, galloles, siloles and phospholes via metallacycle transfer is well know to those who practice the art of pharmaceutical and pesticide research. A review of this chemistry is provided by Fagan et al in The Journal Of *The American Chemical Society*, 116, 1880–1889 (1994). The Group IV metallacycle compounds previously known have included substituted metallacycles with alkyl or silyl alkyl groups.

The use of main group heterocycles as ligands in organometallic complexes useful as olefin polymerization catalysts is disclosed by Sone et al in U.S. Pat. No. 5,434,116. Sone et al exemplify the use of catalysts having heterocyclic, phosphorus containing ligands ("phosphole" or "phospholyl" catalysts) which are activated by alumoxanes or certain "substantially non-coordinating anions", to produce polyethylene having a desirable molecular weight distribution-although these catalysts are not particularly active. Subsequent disclosures of the use of phosphole catalysts have been made in Patent Cooperation Treaty (PCT) application 95/04087 (deBoer et al, to Shell); European Patent Office (EPO) application 617,052 (Aoki et al, to Asahi) and EPO 741,145 (Katayama etal, to Sumitomo).

The use of alumoxanes and/or substantially non-coordinating anions as cocatalysts is well known to those skilled in the art of olefin polymerization and is typically associated with the use of so-called metallocene and/or half metallocene catalysts.

The combination of a metallocene catalyst (i.e. a catalyst having two cyclopentadienyl ligands) and an alumoxane cocatalyst is disclosed by Kaminsky etalin U.S. Pat. Nos. 4,404,344 and 4,542,199.

Hlatky and Turner subsequently made the important discovery that substantially non-coordinating anions may also function as cocatalysts for metallocene catalysts, as disclosed in U.S. Pat. No. 5,198,401. Other Hlatky and Turner patents of relevance to these cocatalysts include U.S. Pat. Nos. 5,153,157 and 5,407,884.

Half metallocene complexes (those with only one cyclopentadienyl ligand) have also been discovered to be versatile olefin polymerization catalysts.

Most notable is the bridged dianionic cyclopentadienyl-heteroatom ligand reported by Bercaw et al ("Bercaw ligand") at the Third Chemical Congress in North America (June 1988).

The use of a Group IV metal complex having a "Bercaw ligand" in combination with an alumoxane cocatalyst for olefin polymerization is disclosed by Canich in U.S. Pat. No. 5,055,438. Other patents which are relevant to the Bercaw ligand/alumoxane combination include U.S. Pat. Nos. 5,057,475; 5,096,867 and 5,227,440.

The use of a Group IV metal complex of the Bercaw ligand in combination with a substantially non-coordinating anion as a cocatalyst is disclosed by Stevens et al in U.S. Pat. No. 5,132,380. Other patents which are relevant to this catalyst/cocatalyst combination include U.S. Pat. Nos. 5,374,696 and 5,399,635.

The use of a metallocene or half metallocene in olefin polymerizations generally results in the production of polyolefins having both desirable properties (e.g. optical clarity, high impact strength, organoleptics) and undesirable properties (particularly poor processability, which is thought to be caused by the very narrow molecular weight distribution of most polymers produced this way).

An olefin polymerization catalyst which provides the desirable features of both the metallocene (or half metallocene) catalyst and the "phosphole" catalyst would represent a desirable addition to the art. [Conversely, an olefin polymerization catalyst which displays the undesirable features of both wou ld be nothing more tha n an academic curiosity!] The preparation of an organometallic complex having a simple cyclopentadienyl ligand and a simple heterocyclic ligand involves only trivial chemistry. Such organometallics have been prepared, tested, and reported to be comparatively uninteresting polymerization catalysts (see Janiak et al, *Journal of Organometallic Chemistry* 501 (1995) pp. 219–34).

The question whether a "bridged, divalent phosphole heteroatom ligand" (analogous to the Bercaw ligand) would be useful in the preparation of olefin polymerization catalysts was heretofore unanswered, perhaps because the use of conventional organometallic synthetic methods did not readily lead to the desired ligand.

SUMMARY OF THE INVENTION

We have discovered synthetic methods to prepare new metallacycles. These new metallacycles are useful for the preparation of new main group heterocycles. Certain of these new main group heterocycles are useful in the preparation of a dianionic, bridged heterocyclic ligands (which are analogous to the Bercaw ligand). We have also discovered new organometallic complexes having a dianionic bridged heterocycle ligand which are excellent polymerization catalysts.

Thus, in one embodiment of the invention there is provided a family of metallacycles:

A metallacycle of a Group IV metal selected from Ti, Zr and Hf, said metallacycle having:
(a) two cyclopentadienyl ligands;
(b) a dianionic, cyclic, unsaturated ligand having four carbon atoms, wherein one carbon atom adjacent to said Group IV metal is substituted with a monohalogenated metalloid group.

A preferred member of this metallacycle family is the zirconacycle illustrated below (namely (bis(η5-cyclopentadien-1-yl)(1-chlorodimethylsilyl-2,3,4-trimethyl-1,3-butadienyl-1,4-diyl) zirconium, also referred to herein as zirconacycle 1):

formula 1

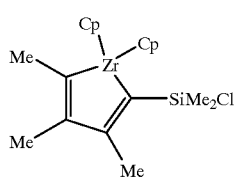

wherein Cp is a cyclopentadienyl ligand and Me is methyl.

The chlorodimethylsilyl ("ClMe$_2$Si") substituent on zirconacycle 1 facilitates the subsequent preparation of heterocycles having complex substituent arrangements.

In another embodiment this invention provides a heterocycle family according to the formula:

formula 2

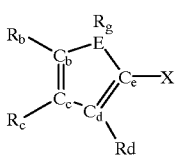

wherein:

$C_b$, $C_c$, $C_d$ and $C_e$ are carbon atoms;

$R_b$, $R_c$ and $R_d$ are hydrogen or optional non-interfering substituents;

E is selected from P, As, Sb and Bi;

Rg is a leaving group bonded to E; and

X is defined by the formula

wherein:

h is a halogen atom;

m is selected from Si, Ge and Sn;

$R_e$ and $R_f$ are non-interfering groups bonded to m; and m is bonded to h and m is bonded to $C_e$.

A preferred member of this heterocycle family is 2-chlorodimethylsilyl-1-phenyl-3,4,5-trimethylphosphole ("1P2CTMP").

In another embodiment the invention provides another family of heterocycles defined by the formula:

formula 3

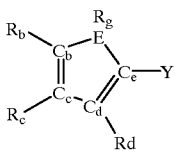

wherein:

$R_g$, E, $C_b$, $C_c$, $C_d$, $C_e$, $R_b$, $R_d$ and $R_d$ are as defined above with reference to formula 2 and Y is defined by the formula:

wherein:

$R_e$, $R_f$ and m are as defined above with reference to formula 2;

K comprises a heteroatom selected from N, P, S or O with the provisos that:

(i) said atom m is bonded to $C_e$;

(ii) said atom m is bonded to said heteroatom;

(iii) K contains a leaving group bonded to said heteroatom; and (iv) K may contain up to 40 non-hydrogen atoms when said heteroatom is N or P.

A preferred member of this heterocycle family is 2-[(tert-butylamino)dimethylsilyl]-1-phenyl-3,4,5-trimethylphosphole ("1P2TBADMSTMP"). In 1P2TBADMSTMP, the substituent Y is (tertiary-butyl amino) (dimethyl) silyl which is bonded to $C_e$ via the Si atom. The tertiary butyl amino group contains a labile H atom which facilitates further manipulation of this molecule.

The invention also provides an organometallic complex useful in olefin polymerization, where the complex has a dianionic bridged heterocyclic ligand as defined by the formula:

formula 4

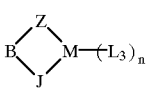

wherein:

M is a metal selected from Sc, Zr, Hf, Ti, and V;

J-B-Z is a dianionic, bridging ligand bonded to M;

B is a bridging component which is bonded to said J and said B, wherein B is defined by the formula:

where m, $R_e$ and $R_f$ are as defined above with reference to formula 2;

J comprises a heteroatom selected from N, P, O and S; wherein said heteroatom is bonded to B and bonded to M; and $L_3$ is a non-interfering ligand bonded to m and n is 1, 2 or 3 depending on the valence of M. (For example, n is 2 when the metal M is Zr(IV), Hf(IV) or Ti(IV) and n is 1 when M is Sc(III) or Ti(III).)

The preferred organometallic complex is 1-[(tert-butylamido)dimethylsilyl]-2,3,4-trimethylphospholyl titanium dichloride.

Although the above formula shows a monomeric molecule, it will be appreciated by those skilled in the art that certain of the organometallic complexes encompassed by the formula may exist in oligomeric form, as may be determined by x-ray crystallography.

The invention further provides an olefin polymerization process which employs the above-described organometallic complex.

DETAILED DESCRIPTION

For clarity, this description is set out in two sections; namely one section which describes preferred chemical syntheses and the preferred metallacycles, heterocycles and organometallic catalyst components produced according to these syntheses; and a second section relating to olefin polymerizations.

The following conventional abbreviations have been used: g for grams; mL for milliliters; mol/L for moles per liter; mmol for millimole; L for liter; mg for milligrams; psig for pounds per square inch gauge; cc for cubic centimeters; hr for hours; and min for minutes.

PART A: Chemical Syntheses

1. Preparation of Metallacycles, Particularly Zirconacycle 1

The preparation of zirconacycle 1 preferably employs chloro(dimethyl)(propynyl)silane ("CDPS"). The procedures used to prepare CDPS are thought to be new and are, therefore, described below:

1.1 Preparation of CDPS:

To a solution of dichlorodimethylsilane (60 mL, 495 mmol) in ether (75 mL) at −20° C. was added a tetrahydrofuran ("THF") solution of propynylmagnesium bromide (200 mL, 0.5 M, 100 mmol). Addition was completed over 30 minutes and then the reaction was allowed to warm to room temperature. The solvent and excess silane were distilled off at ambient pressure and the residue filtered to remove solids. The resulting oil was distilled at ambient pressure and the residue filtered to remove solids. The oil was then distilled at ambient pressure and the fraction boiling between 90–120° C. was isolated. Redistillation gave pure product. Yield, 4.654 g. Proton nuclear magnetic resonance analysis using deutero toluene ($C_7D_8$) as solvent ("1H NMR") showed: 1H NMR ($C_7D_8$): 1.38 (3H), 0.391 (6H).

1.2 Preparation of bis(η5-cyclopentadien-1-yl)(1-chlorodimethylsilyl-2,3,4-trimethyl-1,3-butadienyl-1,4-diyl) zirconium [or "Zirconacycle 1"]:

To a slurry of Schwartz's Reagent ($Cp_2ZrHCl$, 3.802 g, 14.74 mmol) in methylene chloride (50 mL) at 0° C. was added 2-butyne (2.5 mL, 1.72 g, 32 mmol). The reaction was allowed to warm to room temperature and after 30 minutes a clear solution had formed. The solvent and excess butyne were removed in vacuo and the residues dissolved in THF (30 mL). The solution was cooled to −78° C. and a solution of methyl lithium in ether (1.4M, 10.5 mL, 15 mmol) was added. After 15 minutes chloro(dimethyl)(propynyl)silane (1.955 g, 14.7 mmol) was added and the reaction mixture allowed to warm to room temperature. During warming gas evolution was apparent. The reaction was stirred at room temperature for 45 minutes, at 45° C. for 2 hours and then at room temperature overnight. The solvent was removed in vacuo and residues treated with hexane (50 mL). The reaction mixture was then filtered and the filtrate concentrated until crystals started to form. The reaction was then stored at −15° C. for two days. The mother liquor was cannulated away and the orange crystals dried in vacuo. Yield, 4.2 g. 1H NMR ($C_7D_8$): 6.01 (10H), 1.78 (3H), 1.65 (3H), 1.53 (3H), 0.50 (6H).

Zirconacycle 1 is a preferred member of a metallacycle family defined by the aforementioned formula 1.

These metallacycles are novel, particularly with respect to the halogen atom in substituent X of the above formula. It will be appreciated by those skilled in the art that the present metallacycles will be useful reagents for the synthesis of main group heterocycles.

The zirconacycles are the preferred metallacycles. The most preferred zirconacycle is the one in which X is $ClMe_2Si$ (i.e. zirconacycle 1).

2. Preparation of Heterocycles, Particularly 2-chlorodimethylsilyl-1-phenyl-3,4,5-trimethylphosphole ("1P2CTMP")

Zirconacycle 1 (2.11 g, 5.18 mmol) and phenylphosphine dichloride (0.926 g, 5.18 mmol) and toluene (40 mL) were combined and heated to reflux for three hours. The reaction was allowed to cool and the solvent was removed in vacuo. Hexane (50 mL) was added and the reaction mixture cooled to 0° C. Subsequent filtration and removal of the solvent yielded a dark orange oil. This was further purified by a second hexane extraction to remove $Cp_2ZrCl_2$. Yield, 1,38 g. 1H NMR ($C_7D_8$): 7.27 (m, 2H), 7.00 (m, 3H), 2.17 (d, J=4.4 Hz, 3H), 1.81 (d, J=11.6 Hz, 3 H), 1.66 (3H), 0.46 (3H), 0.41 (3H).

1P2CTMP is a preferred member of a novel heterocycle family defined by the aforementioned formula 2.

Referring to formula 2, the "optional non-interfering substituents" encompassed by the groups $R_b$, $R_c$ and $R_d$ are not particularly important to the success of this invention. It will be appreciated that skilled organometallic chemists are able to widely manipulate the molecule illustrated by formula 1 by altering these substituents $R_b$, $R_c$ and $R_d$. A list of the most obvious substituents includes the group consisting of $C_1$–$C_{20}$ hydrocarbyl radicals; substituted $C_1$–$C_{20}$ hydrocarbyl radicals wherein one or more hydrogen atoms is replaced by a halogen radical, an amido radical, a phosphido radical, an alkoxy radical or a radical containing a Lewis acidic or basic functionality; $C_1$–$C_{20}$ hydrocarbyl-substituted metalloid radicals wherein the metalloid is selected from the Group IV A of the Periodic Table of Elements; and halogen radicals, amido radicals, phosphido radicals, alkoxy radicals, alkylborido radicals, or a radical containing Lewis acidic or basic functionality; or a ring in which two adjacent R-groups are joined forming $C_4$–$C_{20}$ ring to give a saturated or unsaturated polycyclic ligand. The groups $R_e$ and $R_f$ are any non-interfering group ligands which will bond to the Si (or Ge or Sn) atom while still allowing the bond to the halogen. (i.e. The $R_e$ and $R_f$ groups are not important to this invention. $R_e$ and $R_f$ may optionally be bonded to each other. Preferred examples of $R_e$ and $R_f$ include halogens, hydrocarbyl and halo-hydrocarbyl groups. It is especially preferred that both $R_e$ and $R_f$ are methyl.)

As used herein, the term "leaving group" is intended to convey its conventional meaning to organometallic chemists—i.e. a fragment or group which may be cleaved off in a manner which facilitates further manipulation of the subject molecule. Examples of suitable leaving groups bonded to E include a single H atom (which may, for example, be cleaved off with an alkyl lithium reagent), trialkyl (or triaryl) tin, trialkyl (or triaryl) Si; Group IA or Group IIA atoms, or aryl, with aryl (especially phenyl) being preferred.

The preferred heterocycles are those in which the Rg group is aryl (especially phenyl); those in which X is $ClMe_2Si$; and those in which E is a phosphorus atom. 1P2CTMP is particularly useful in the preparation of organometallic complexes which are components of olefin polymerization catalyst systems.

3. Preparation of Heterocycles, Particularly 2-[(tert-butylamino)dimethylsilyl]-1-phenyl-3,4,5-trimethylphosphole ("1P2TBADMSTP")

To a solution of 1P2CTMP from part 2 above (1.358 g, 4.61 mmol) in THF (30 mL) at −78° C. was added tertiary-butylamine (1.3 mL, 12.4 mmol). A white precipitate started to form immediately. The reaction was removed from the cold bath and allowed to warm to room temperature. After one hour the THF and other volatiles were removed in vacuo and hexane (10 mL) added. This hexane was removed in vacuo to ensure all THF was removed and fresh hexane (50 mL) added. The reaction was filtered, the solvent removed in vacuo and the resulting orange oil isolated. Yield, 1.483 g. 1H NMR ($C_7D_8$): 7.3 (m, 2H), 7.0 (m, 3H), 2.25 (d, 3H), 1.9 (d, 3H), 1.78 (3H), 1.08 (9H), 0.27 (6H).

1P2TBADMSTP is a preferred member of a novel family of heterocycles defined by the aforedescribed formula 3. In general, the preferred heterocycles are those in which the $R_g$ leaving group is aryl (especially phenyl); E is a phosphorus atom and Y includes the above described metalloid (which is most preferably a dialkyl substituted Si atom, especially dimethyl silyl or $Me_2Si$), a ligand fragment containing a heteroatom which is bonded to the metalloid and which includes a leaving group.

When the heteroatom is O or S (which are both divalent), the preferred leaving group is a single H atom bonded directly to the heteroatom. When the heteroatom is N or P (which are trivalent), the group Y may further include up to 40 non-hydrogen atoms (e.g. in the form of a non-leaving substituent on the heteroatom). Suitable leaving groups include an H atom; trialkyl tin; triaryl tin; trialkyl Si; trialkyl Ge; triaryl Ge; Group IA or Group IIA elements. It is preferred that Y is (tertiary butyl amino) dimethyl silyl (i.e. that the heteroatom is N; the N be substituted with a tertiary butyl group and that an H atom be the leaving group).

4. Preparation of Organometallic Complexes Having a Dianionic Bridging Heterocyclic Ligand, Particularly 1-[(tert-butylamido)dimethylsilyl]-2,3,4-trimethylphospholyl titanium dichloride [or "SiTiNP", or "(C$_4$Me$_3$P)SiMe$_2$t-BuNTiCl$_2$"]

A convenient synthesis of SiTiNP employs a novel tin substituted heterocycle, 2[((trimethylstannyl) (tert-butyl) amino)dimethylsilyl]-1-trimethylstannyl-3,4,5-trimethylphosphole ("SnTMP") . As SnTMP is novel, a method to prepare it is described below.

4.1 Preparation of SnTMP:

A solution of 1P2TBADMSTP from part 3 above (1.465 g, 4.4 mmol) in THF (30 mL) was added to lithium foil (163 mg, 143 mmol) at room temperature and the reaction was stirred for 3 hours. The resulting dark red solution was then cannulated from the excess lithium into a solution of trimethyltinchloride (2.04 g, 10 mmol) in THF (20 mL) at −78° C. The reaction was allowed to warm to room temperature. After one hour the solvent was removed in vacuo and residues analyzed by 1 H NMR spectroscopy. The NMR spectrum showed that the distannyl had formed essentially quantitatively. 1H NMR (C$_7$D$_8$): 2.48 (d, 3H), 2.2 (3H), 1.92 (3H), 1.26 (9H), 0.48, 0.38.

4.2 Preparation of SiTiNP:

A solution SnTMP (from the previous preparation, 4.4 mmol) in toluene (30 mL) was added to a toluene solution of titanium tetrachloride at 0° C. The reaction turned dark red immediately and it was left to stir overnight. The toluene and other volatiles were removed in vacuo to leave a red oil. A 1H NMR spectrum of this material showed it to be a mixture of products. The oil was dissolved in toluene (50 mL), filtered and then heated to 100° C. for 1 hour. The volatiles were then removed in vacuo to leave an orange/red crystalline solid. The solid was dissolved in hexane (40 mL) and the solution filtered. The hexane was removed in vacuo and the product dissolved in pentane (40 mL). After filtration, the pentane solution was placed in a freezer at −30° C. for two days. Deep red crystals formed and these were isolated by decanting the mother liquor and washing with a little pentane. Yield, 728 mg. 1H NMR (C$_7$D$_8$): 2.22 (d, J=10 Hz, 3H), 2.04 (3H), 2.01 (3H), 1.36 (9H), 0.57 (3H), 0.43 (3H).

SiTiNP is a preferred member of a family or oganometallic complexes defined by the aforedescribed formula 4.

In formula 4, reference is made to a "non-interfering ligand" which is a term used herein to refer to a ligand which does not interfere with the use of the organometallic complex (for example, in olefin polymerizations). The non-interfering ligand is preferably a halide (especially chlorine or bromine), hydrogen or methyl, though it will be recognized by those skilled in the art that many other trivial ligands including alkyl alkoxy, aryl and aryloxy ligands having up to 20 carbon atoms (and halo substituted derivatives thereof), amides and silyls are also non-interfering.

PART B-1: Polymerization

The polymerization process of this invention is conducted in the presence of a catalyst which is an organometallic complex according to the aforedefined formula 4 and an "activator or cocatalyst". The terms "activator" or "cocatalyst" may be used interchangeably and refer to a catalyst component which combines with the organometallic complex to form a catalyst system that is active for olefin polymerization.

Preferred cocatalysts are the well known alumoxane (also known as aluminoxane) and ionic activators.

The term "alumoxane" refers to a well known article of commerce which is typically represented by the following formula:

R$_2$'AlO(R'AlO)$_m$AlR$_2$' where each R' is independently selected from alkyl, cycloalkyl, aryl or alkyl substituted aryl and has from 1–20 carbon atoms and where m is from 0 to about 40 (especially from 5 to 10). The preferred alumoxane is methylalumoxane or "MAO" (where each of the R' is methyl).

Alumoxanes are typically used in substantial molar excess compared to the amount of metal in the catalyst. Aluminum:transition metal molar ratios of from 10:1 to 10,000:1 are preferred, especially from 50:1 to 500:1.

As used herein, the term "substantially non-coordinating anion" is meant to refer to the well known cocatalyst systems described in the aforementioned Hlatky and Turner U.S. patent references, and carbonium, sulfonium and oxonium analogues of such ionic cocatalysts which are disclosed by Ewen in U.S. Pat. No. 5,387,568. In general, these ionic cocatalysts may be defined by the formulae:

[C$^+$][A$^-$] or [A$^-$]

where C is a poorly coordinating cation which most preferably is non-interfering towards the catalyst and A is an anion which weakly coordinates to a cationic form of the catalyst. Referring to the above formula, C may or may not contain an active proton (e.g. trimethyl ammonium, tributylammonium; N,N-dimethyl anilinium, carbonium, oxonium or sulfonium) and A is a bulky, labile anion (such as tetraphenyl borate, tetra(pentafluorophenyl) borate and anions containing more than one boron atom). The preferred of these activators are tris(pentafluorophenyl) boron (which can generate the borane upon reaction with the organometallic catalyst complex), [triphenyl methyl][tetrakis (pentafluorophenyl) boron] and [N,N-dimethyl anilinium] [tetrakis(fluorophenyl) boron].

These activators are typically used in approximately equimolar amounts (based on the transition metal in the catalyst) but lower levels may also be successful and higher levels also generally work (though sub-optimally with respect to the cost-effective use of the expensive activator).

In addition to the catalyst and cocatalyst, the use of a "poison scavenger" may also be desirable. As may be inferred from the name "poison scavenger", these additives may be used in small amounts to scavenge impurities in the polymerization environment. Aluminum alkyls, for example triisobutyl aluminum, are suitable poison scavengers. (Note: some caution must be exercised when using poison scavengers as they may also react with, and deactivate, the catalyst.)

Polymerizations according to this invention may be undertaken in any of the well known olefin polymerization processes including those known as "gas phase", "slurry", "high pressure" and "solution".

The use of a supported catalyst is preferred for gas phase and slurry processes whereas a non-supported catalyst is preferred for the other two.

When utilizing a supported catalyst, it may be preferable to initially support the cocatalyst, then the catalyst (as will be illustrated in the Examples).

The polymerization process according to this invention uses at least one olefin monomer (such as ethylene, propylene, butene, hexene) and may include other monomers which are copolymerizable therewith (such as other alpha olefins, preferably butene, hexene or octene, and under certain conditions, dienes such as hexadiene isomers, vinyl aromatic monomers such as styrene or cyclic olefin monomers such as norbornene).

It is especially preferred that the polymerization process utilize a major portion of ethylene monomer and a minor portion of an alpha olefin comonomer selected from butene, hexene and octene so as to produce a linear low density polyethylene ("LLDPE") product.

Our experiments have shown that LLDPEs produced using the present catalyst have exceptionally high molecular weight. This is particularly advantageous for solution polymerization (in that it is usually desirable to undertake solution polymerizations at high temperatures, and higher temperatures usually reduce the molecular weight of the resulting polymer. (Stated another way: the catalysts of this invention allow the use of desirable (high) temperatures in a solution polymerization process.)

The most preferred polymerization process of this invention encompasses the use of the novel catalysts (together with a cocatalyst) in a medium pressure solution process. As used herein, the term "medium pressure solution process" refers to a polymerization carried out in a solvent for the polymer at an operating temperature from 100 to 320° C. (especially from 120 to 220° C.) and a total pressure of from 4 to 20 mega Pascals. Hydrogen may be used in this process to control (reduce) molecular weight. Optimal catalyst and cocatalyst concentrations are affected by such variables as temperature and monomer concentration but may be quickly optimized by non-inventive tests.

Further details concerning the medium pressure polymerization process (and the alternative gas phase, slurry and high pressure processes) are well known to those skilled in the art (and widely described in the open and patent literature).

EXAMPLES

Further details concerning the invention are disclosed by way of the following non-limiting examples.

The examples are set out in two subsections, namely a subsection which illustrates gas and slurry polymerizations and a subsection which illustrates medium pressure solution polymerizations using an unsupported catalyst.

Sub-Section B-1: Gas Phase/Slurry Polymerization

Example G1

Preparation and Ethylene Polymerization of Silica Supported 1-[(tert-butylamido)-dimethylsilyil]-2,3,4-trimethylphospholyl titanium dichloride (or silica supported SiTiNP)
Catalyst Synthesis:

The titanium-containing organometallic complex used in Examples G1 and G2 was prepared as previously described in part 4.2 of Section A.

Commercial methylaluminoxane or "MAO" on granular silica (1.0 g, Witco TA 02794/ HL/04, 23 wt % Al) was suspended in anhydrous toluene (40 mL). A solution of 1-[(tert-butylamido)-dimethylsilyl]-2,3,4-trimethylphospholyl titanium dichloride was prepared in anhydrous hexane (0.033 mol/L) and a volume of 3.0 mL of this solution was added dropwise to a stirred suspension of the MAO on silica. The mixture was allowed to stir overnight and subsequently heated at 45° C. for a period of 2.5 hours. The resulting solid was collected via filtration and washed first with toluene (2×15 mL) and then hexane (2×20 mL). After drying in vacuo for 1 hour, 0.8 grams of a free-flowing powder was obtained. Neutron activation analysis showed a titanium concentration of 0.096 mmol Ti per gram of catalyst.
Polymerization:

Gas phase ethylene homopolymerization of the supported catalyst was conducted by introducing the catalyst (30 mg) into a continuously stirred, 2L pressure vessel under operating conditions of 200 psig ethylene (Praxair, polymerization grade) and at a constant temperature of 90° C. for a period of 1 hr. A seed bed of NaCl (70 g, oven dried at 175° C. for 48 hours), treated in situ with a heptane solution of tri-isobutylaluminum (TIBAl, 1 mL of a 25 wt % solution, Akzo Nobel), was added to the reactor prior to introduction of the catalyst. Upon termination of the reaction and isolation of the polymer, a free-flowing product was obtained in a yield of 12 g, representing a catalyst productivity of 43,300 grams of polyethylene per gram of Ti per hour ("g PE/g Ti×hr"). The polymer, characterized by gel permeation chromatography (GPC), showed a weight average molecular weight of 1,100,000 (Mw) and a polydispersity of 5.5. ("Polydispersity" refers to the value obtained by dividing Mw by the number average molecular weight or "Mn"—i.e. polydispersity equals Mw/Mn.)

Example G2

Ethylene-1-Butene Copolymerization Using Silica Supported 1-[(tert-butylamido)-dimethylsilyl]-2,3,4-trimethylphospholyl titanium dichloride
Polymerization:

Gas phase ethylene -1-butene copolymerization of the supported catalyst was conducted by introducing the catalyst (30 mg) into a continuously stirred, 2L pressure vessel under operating conditions of 200 psig of a continuously supplied 4 mol % mixture of 1-butene in ethylene (Airgas, polymerization grade) and at a constant temperature of 90° C. for a period of 1 hr. A seed bed of NaCl (70 g, oven dried at 175° C. for 48 hours), treated in situ with a heptane solution of tri-isobutylaluminum (TIBAl, 1 mL of a 25 wt % solution, Akzo Nobel), was added to the reactor prior to introduction of the catalyst. Upon termination of the reaction and isolation of the polymer, a free-flowing product was obtained in a yield of 26 g, representing a catalyst productivity of 95,900 g PE/g Ti×hr. The polymer, characterized by gel permeation chromatography (GPC), showed a molecular weight of 1,100,000 (Mw) and a polydispersity of 6.1.

COMPARATIVE EXAMPLES

The comparative examples illustrate that catalysts containing the phosphole ligands disclosed by Sone et al (U.S. Pat. No. 5,434,116) are substantially less active than the catalysts of this invention in the gas phase (co-) polymerization of ethylene.

Comparative Example G1-C

Preparation and Ethylene Polymerization of Silica Supported TetramethylphospholVl Titanium Trichloride
Catalyst Preparation:

Commercial polymethylaluminoxane (MAO) on granular silica (2.0 g, Witco TA 02794/HL/04, 23 wt % Al) was suspended in anhydrous toluene (15 mL). A solution of tetramethylphospholyl titanium trichloride was prepared in anhydrous toluene (25 mL having a concentration of 0.026 mol/L) and this total volume added to a stirred suspension of the MAO on silica. The mixture was allowed to stir overnight. The resulting solid was collected via filtration and washed first with toluene (2×20 mL) and then hexane (2×10 mL). After drying in vacuo, 1.8 g of a free-flowing powder was obtained. Neutron activation analysis showed a titanium concentration of 0.215 mmol Ti per gram of catalyst.
Polymerization Using the same procedure as described in Example 1, 0.3 g of polyethylene was obtained, representing a catalyst productivity of 1, 230 g/g Ti×hr.

Comparative Example G2-C

Preparation and Ethylene Polymerization of Silica Supported Bis-tetramethylphospholyl zirconium dichloride Catalyst Preparation:

The same procedure as described in Comparative Example 1 was used, except that bis-tetramethylphospholyl zirconium dichloride (25 mL having a concentration of 0.016 mol/L) was used in place of tetramethylphospholyl titanium trichloride and that 1.7 g of catalyst was obtained. Neutron activation analysis showed a zirconium concentration of 0.065 mmol Zr per gram of catalyst. Polymerization:

Using the same procedure as described in Example 1, 4.7 g of polyethylene was obtained, representing a catalyst productivity of 20,600 g/g Zr×hr. The polymer, characterized by gel permeation chromatography (GPC), showed a molecular weight of 226,000 (Mw) and a polydispersity of 4.9.

Comparative Example G3-C

Preparation and Ethylene Polymerization of Silica Supported Tetramethylphospholyl(cyclopentadienyl) zirconium-dichloride Catalyst Preparation:

The same procedure as described in Comparative Example 1 was used, except that tetramethylphospholyl (cyclopentadienyl) zirconium dichloride (35 mL having a concentration of 0.017 mol/L) was used in place of tetramethylphospholyl titanium trichloride, 2.8 g of the MAO on silica were used and that 2.7 g of catalyst was obtained. Neutron activation analysis showed a zirconium concentration of 0.140 mmol Zr per gram of catalyst.

Polymerization:

Using the same procedure as described in Example 1, 4.8 g of polyethylene was obtained, representing a catalyst productivity of 20,800 g/g Zr×hr. The polymer, characterized by gel permeation chromatography (GPC), showed a molecular weight of 209,000 (Mw) and a polydispersity of 6.9.

EXAMPLE

Example SL-1

Slurry Polymerization:

The organometallic complex "$(C_4Me_3P)SiMe_2$ t-BuNTiCl$_2$" was prepared as previously described in part 4.2 of Section A.

Slurry polymerizations were carried out in a temperature controlled reactor at 35° C. at an ethylene pressure of 10 psig. 300 mL of purified cyclohexane was first transferred to the reactor followed by the addition of a commercially available methylalumoxane ("PMAO-IP", Akzo-Nobel) (1.8 mL of 12.9 wt % Al) and was then stirred for 5 minutes. The catalyst, $[(C_4Me_3P)SiMe_2$ t-BuN]TiCl$_2$ ($15.2 \times 10^{-6}$ moles dissolved in 0.4 mL of hexane) was then added and the reactor pressurized to 10 psig with ethylene. Polymerization was allowed to continue to 30 minutes at which time the pressure was vented (to prevent further reaction) and the polymer was recovered by evaporation of the solvent. Reactor temperature and ethylene consumption were monitored during the reaction. The polymer yield was 2.19 g giving an activity of 0.29 kg PE/(mmol Ti×hr). (Note: this is a slurry polymerization (as the temperature was not hot enough to dissolve the polymer) using an unsupported catalyst.)

PART B-2: Solution Polymerization

All the polymerization experiments described below were conducted on a continuous solution polymerization reactor. The process is continuous in all feed streams (solvent, monomers, catalyst and cocatalyst) and in the removal of product. All feed streams were purified prior to addition to the reactor. All components were stored and manipulated under an atmosphere of purified nitrogen.

All the experiments below were conducted in a reactor of 71.5 cc internal volume. In each experiment the volumetric feed to the reactor was kept constant and as a consequence so was the reactor residence time.

The catalyst and cocatalyst solutions were pumped to the reactor independently and there was no pre-contact between the catalyst (or "organometallic complex") component and the cocatalyst component. Because of the low solubility of the catalyst and the MAO in cyclohexane, solutions were prepared in toluene. The catalyst was activated in situ (i.e. in the polymerization reactor) at the reaction temperature in the presence of the monomers. The polymerizations were carried out in cyclohexane at a pressure of 1500 psig. Ethylene is supplied to the reactor by a calibrated thermal mass flow meter and is dissolved in the reaction solvent prior to the polymerization reactor. If comonomer is used it is also premixed with the ethylene before entering the polymerization reactor. Under these conditions the ethylene conversion is a dependent variable which is controlled by such factors as the catalyst concentration, reaction temperature and catalyst activity.

The internal reactor temperature is monitored by a thermocouple in the polymerization medium and can be controlled at the required set point to +/−0.5° C. Down stream of the reactor the pressure is reduced from the reaction pressure (1500 psig) to atmospheric. The solid polymer is then recovered as a slurry in the condensed solvent and dried by evaporation before analysis.

The ethylene conversion is determined by a dedicated on line gas chromatograph.

Polymer Analysis:

GPC analysis was carried out on a commercial instrument (Waters 150C GPC) using 1,2,4-trichlorobenzene as the mobile phase at 140° C. The samples were prepared by dissolving the polymer in the mobile phase solvent in an external oven at 0.1% (weight/volume), (w/v) and were run without filtration. Molecular weights are expressed as polyethylene equivalents with a relative standard deviation of 2.9% and 5.0% for the number average (Mn) and weight average (Mw).

Melt index (MI) measurements were conducted according to ASTM method D-1238–82.

Polymer densities were measured on pressed plaques (ASTM D-1928–90) with a densitometer.

Example S-1

The organometallic complex "$(C_4Me_3P)SiMe_2$ t-BuNTiCl$_2$" used in Examples S-1 to S-6 was prepared as previously described in part 4.2 of Section A.

$[(C_4Me_3P)SiMe_2$ t-BuN]TiCl$_2$ was added to the reactor at $37 \times 10^{-6}$ mol/l along with a commercially available MAO (PMAO-IP, Akzo-Nobel) at Al/Ti=400 (mol/mol). The reaction temperature was 140° C. and 1 gram/min of ethylene was continuously added to the reactor. An ethylene conversion of 82.8% was observed (see Table 1).

Example S-2

Conditions were as in example 1 except that 0.63 mL/min of 1-octene was also added to the reactor. An ethylene conversion of 82.0% was seen (see Table 1).

Example S-3

Conditions were as in example 1 except that a polymerization temperature of 160° C. was used. An ethylene conversion of 79.4% was seen (see Table 1).

Example S-4

Conditions were as in example 3 except that 2.1 grams/min of ethylene was used. An ethylene conversion of 86.3% was seen (see Table 1).

Example S-5

Conditions were as in example 3 except that 2.0 grams/min of ethylene and 3.0 mL/min of 1-octene was used. An ethylene conversion of 85.2% was seen (see Table 1).

Example S-6

$(C_4Me_3P)SiMe_2$ t-$BuNTiCl_2$ was added to the reactor at $37 \times 10^{-6}$ mol/l along with butylethylmagnesium $185 \times 10^{-6}$ mol/l, Mg/Ti=5 (mol/mol) and $Ph_3C\ B(C_6F_5)_4$ $37 \times 10^{-6}$ mol/l B/Ti=1 (mol/mol). The reaction temperature was 160° C. and 2.1 gram/min of ethylene was continuously added to the reactor. An ethylene conversion of approximately 40% was observed. Subsequent analysis of the monomer indicated an extremely high amount of impurities were present which is the probably reason for the low conversion level observed.

COMPARATIVE EXAMPLES

The following comparative examples show that complexes which include the phosphole-containing ligand taught by Sone et al in U.S. Pat. No. 5,434,116 are extremely poor catalysts in the medium pressure process for the (co-)polymerization of ethylene.

Comparative Example S-1-C $(C_4Me_4P)_2ZrCl_2$ was added to the reactor at $37 \times 10^{-6}$ mol/l along with a commercially available methylalumoxane ("MMAO-3", Akzo-Nobel) at Al/Ti=400 (mol/mol). The reaction temperature was 160° C. and 1 gram/min of ethylene was continuously added to the reactor. An ethylene conversion of 36.6% was observed (see Table 2).

Comparative Example S-2-C $(C_4Me_4P)_2ZrCl_2$ was added to the reactor at $37 \times 10^{-6}$ mol/l along with MMAO-3 (Akzo-Nobel) at Al/Ti=400 (mol/mol). The reaction temperature was 140° C. and 1 gram/min of ethylene was continuously added to the reactor. An ethylene conversion of 56.4% was observed (see Table 2).

Comparative Example S-3-C $(C_4Me_4P)_2ZrCl_2$ was added to the reactor at $74 \times 10^{-6}$ mol/l along with MMAO-3 (Akzo-Nobel) at Al/Ti=400 (mol/mol). The reaction temperature was 140° C. and 1 gram/min of ethylene was continuously added to the reactor. An ethylene conversion of 75.0% was observed (see Table 2).

Comparative Example S-4-C $(C_4Me_4P)TiCl_3$ was added to the reactor at $37 \times 10^{-6}$ mol/l along with MMAO-3 (Akzo-Nobel) at Al/Ti=400 (mol/mol). The reaction temperature was 140° C. and 1 gram/min of ethylene was continuously added to the reactor. No ethylene conversion was observed (see Table 2).

Comparative Example S-5-C $(C_4Me_4P)TiCl_3$ was added to the reactor at $148 \times 10^{-6}$ mol/l, along with MMAO-3 (Akzo-Nobel) at Al/Ti=400 (mol/mol). The reaction temperature was 140° C. and 1 gram/min of ethylene was continuously added to the reactor. An ethylene conversion of 24.0% was observed (see Table 2).

Comparative Example S-6-C $(C_4Me_4P)ZrCl_3$ was added to the reactor at $42 \times 10^{-6}$ mol/l along with MMAO-3 (Akzo-Nobel) at Al/Ti=356 (mol/mol). The reaction temperature was 140° C. and 1 gram/min of ethylene was continuously added to the reactor. An ethylene conversion of 10.0% was observed (see Table 2).

Comparative Example S-7-C $(C_5Me_5)_2ZrCl_2$ was added to the reactor at $37 \times 10^{-6}$ mol/l along with MMAO-3 (Akzo-Nobel) at Al/Ti=400 (mol/mol). The reaction temperature was 160° C. and 1 gram/min of ethylene was continuously added to the reactor. An ethylene conversion of 35.6% was observed (see Table 2).

TABLE 1

| Example | Total flow to reactor (mL/min) | Catalyst concentration (mol $\times 10^6$) | Ethylene conversion (%) | Calculated polymerization rate (l/mmol × min) | Polymer Mn $\times 10^{-3}$ | Polymer Mw $\times 10^{-3}$ | Polymer density (g/cc) | Polymer melt index |
|---|---|---|---|---|---|---|---|---|
| S-1 | 27.0 | 37.0 | 82.8 | 50.0 | — | — | — | — |
| S-2 | 27.0 | 37.0 | 82.0 | 47.5 | — | — | — | — |
| S-3 | 27.0 | 37.0 | 79.4 | 40.2 | — | — | — | — |
| S-4 | 27.0 | 37.0 | 86.3 | 65.5 | 18 | 50 | 0.966 | 10.6 |
| S-5 | 27.0 | 37.0 | 85.2 | 58.2 | 14 | 38 | 0.943 | 29.6 |

TABLE 2

| Example | Total flow to reactor (mL/min) | Catalyst concentration (mol × 10$^6$) | Ethylene conversion (%) | Calculated polymerization rate (l/mmol × min) | Polymer Mn × 10$^{-3}$ | Polymer Mw × 10$^{-3}$ |
|---------|---|---|---|---|---|---|
| S-1-C | 27.0 | 37.0 | 36.6 | 5.9 | — | — |
| S-2-C | 27.0 | 37.0 | 56.4 | 13.2 | — | — |
| S-3-C | 27.0 | 74.0 | 75.0 | 15.3 | — | — |
| S-4-C | 27.0 | 37.0 | 0.0 | 0.0 | — | — |
| S-5-C | 27.0 | 148.0 | 24.0 | 0.8 | — | — |
| S-6-C | 27.0 | 42.0 | 10.0 | 1.0 | — | — |
| S-7-C | 27.0 | 37.0 | 35.6 | 5.6 | 1.8 | 7.5 |

What is claimed is:

1. An organometallic complex useful as a component of an olefin polymerization catalyst system, as defined by the formula:

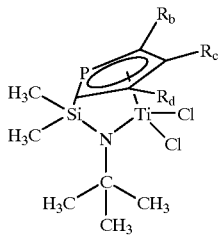

wherein each of $R_b$, $R_c$ and $R_d$ is a hydrocarbyl radical having from 1 to 20 carbon atoms.

2. The organometallic complex 1-[(tertiarybutylamido)dimethylsilyl]-2,3,4-trimethylphospholyl titanium dichloride, according to claim 1 and as defined by the formula:

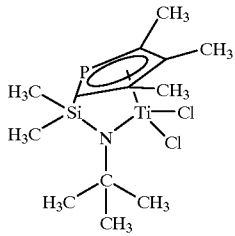

3. A catalyst system for olefin polymerization comprising:

(a) an organometallic complex according to claim 1, and
(b) an activating cocatalyst.

4. A catalyst system according to claim 3 wherein said activating cocatalyst is selected from an alumoxane and a substantially non-coordinating anion.

5. A catalyst system according to claim 3 which further includes a catalyst support.

6. A catalyst system according to claim 5 wherein said catalyst support is silica and wherein said activating cocatalyst is first deposited on said support, followed by said organometallic complex.

7. A catalyst system according to claim 6 wherein said activating cocatalyst is an alumoxane and the mole ratio of aluminum in said alumoxane to the metal M in said organometallic complex is from 10:1 to 100:1.

8. A process for olefin polymerization comprising contacting one or more polymerizable olefin monomers with a catalyst system according to claim 3.

9. A process according to claim 8 wherein said monomers consist of a major portion of ethylene and a minor portion of at least one of butene, hexene and octene.

10. A process to prepare linear low density polyethylene by the medium pressure solution copolymerization of ethylene and a comonomer selected from butene and octene, said process comprising contacting a catalyst system according to claim 3 with said ethylene and comonomer in a solvent for said linear low density polyethylene at a temperature of from 100° C. to 320° C. and a pressure of from 4 to 20 mega Pascals.

11. Linear low density polyethylene produced according to the process of claim 10.

* * * * *